United States Patent [19]

Brunet et al.

[11] Patent Number: 5,189,213

[45] Date of Patent: Feb. 23, 1993

[54] PROCESS FOR THE CARBONYLATION OF ACRYLIC ACID

[75] Inventors: Jean-Jacques Brunet, Portet Sur Garonne; Elisabeth Passelaigue, Messeix, both of France

[73] Assignee: Rhone-Poulenc Chimie, Cedex, France

[21] Appl. No.: 592,027

[22] Filed: Oct. 2, 1990

[30] Foreign Application Priority Data

Oct. 2, 1989 [FR] France .................. 89 13055

[51] Int. Cl.$^5$ .................. C07C 51/10
[52] U.S. Cl. .................. 562/517
[58] Field of Search .................. 562/517

[56] References Cited

U.S. PATENT DOCUMENTS

| | | | |
|---|---|---|---|
| 2,604,490 | 7/1952 | Reppe . | |
| 2,739,169 | 3/1956 | Hagemeyer, Jr. | 562/522 |
| 2,801,263 | 7/1957 | Hasek et al. | 562/517 |
| 3,341,578 | 9/1967 | Vitcha et al. | 562/517 |
| 3,646,131 | 2/1972 | Ikarasi et al. . | |
| 3,661,949 | 5/1972 | Fenton . | |

FOREIGN PATENT DOCUMENTS

| | | |
|---|---|---|
| 765969 | 6/1953 | Fed. Rep. of Germany . |
| 1133359 | 3/1956 | Fed. Rep. of Germany . |
| 1006849 | 9/1957 | Fed. Rep. of Germany . |

OTHER PUBLICATIONS

Chemical Abstracts, vol. 88, No. 7, Feb. 1978, Abstract No. 50294m.

*Primary Examiner*—Arthur C. Prescott
*Attorney, Agent, or Firm*—Finnegan, Henderson, Farabow, Garrett and Dunner

[57] ABSTRACT

A process for the preparation of methylmalonic acid wherein acrylic acid is carbonylated using carbon monoxide and water in a basic solution and in the presence of an iron carbonyl derivative. Methylmalonic acid is used for the preparation of pterosine C or in the formulation of special coatings.

19 Claims, No Drawings

PROCESS FOR THE CARBONYLATION OF ACRYLIC ACID

BACKGROUND OF THE INVENTION

1. Field of the Invention

The present invention relates to a process for the catalytic carbonylation of acrylic acid to form methylmalonic acid.

2. Discussion of the Related Art

Methylmalonic acid is used for the preparation of pterosine C as discussed in Canadian Journal of Chemistry 1984, 62, 1945. Methylamalonic acid is also used in the formulation of special coatings intended for the detection of temperature rises as discussed in U.S. Pat. No. 3,995,489. Some metal salts of methylmalonic acid exhibit fungicidal properties as discussed in DE-A-954,462.

SUMMARY OF THE INVENTION

The present invention comprises a process for the preparation of methylmalonic acid whereby acrylic acid is reacted with carbon monoxide and water in a basic solution. The reaction is carried out in the presence of a catalytically effective amount of an iron carbonyl derivative or of a compound capable of forming an iron carbonyl derivative in the reaction mixture.

Preferred iron carbonyl derivatives suitable for use in the invention are iron pentacarbonyl, $Fe_2(CO)_9$ and compounds of the formula $M^{n+}[HFe(CO)_4]_n-$, in which M is an alkali or alkaline-earth metal and n is 1 or 2. The iron carbonyl derivative is more preferably iron pentacarbonyl.

Preferably the basic solution in which the carbonylation reaction takes place consists of, at least partially, an aqueous solution of an alkali metal or alkaline-earth metal hydroxide. Examples of hydroxides which are suitable for use in the invention are sodium hydroxide, potassium hydroxide, lithium hydroxide, calcium hydroxide, barium hydroxide, strontium hydroxide and magnesium hydroxide. Calcium hydroxide is a preferred hydroxide as it allows the pH of the reaction mixture to be maintained between 12 and 13.

The amount of hydroxide in the reaction mixture can vary widely. In general, the amount of hydroxide is from about 0.1 mole to 5 moles of hydroxide per liter of solvent. The amount of hydroxide is preferably from about 0.2 mole to 2 moles per liter of solvent.

The solvent used in the basic solution in the process of the invention may be water alone or may be a mixture of water and a secondary or tertiary alcohol. Secondary or tertiary alcohols suitable for use in the invention are 2-propanol, 2-methyl-2-propanol (tert-butyl alcohol) and 2-butanol. 2-propanol is the preferred alcohol.

When the solvent is a mixture of water and a secondary or tertiary alcohol, the volume ratio of secondary or tertiary alcohol to the water-alcohol mixture is about 10% to 60% and is preferably from about 20% to 50%.

The process is preferably carried out at a temperature greater than or equal to 50° C. The reaction temperature is more preferably less than or equal to 150° C. The reaction temperature is most preferably from about 60° C. to 120° C.

The carbon monoxide preferably has a partial pressure from about 0.1 MPa to 1 MPa (1 to 10 bars) at the reaction temperature. The carbon monoxide partial pressure is more preferably 0.1 MPa to 0.5 MPa (1 to 5 bars) at the reaction temperature.

The amount of acrylic acid in the reaction mixture can vary widely. In general, the amount of acrylic acid is from about 0.1 moles to 5 moles of acrylic acid per liter of solvent; however, this range is not critical.

The amount of iron carbonyl derivative employed as the catalyst can also vary within wide limits. The preferred molar ratio of iron carbonyl derivative, preferably iron pentacarbonyl, to acrylic acid is from about 0.001:1 to 0.30:1. The molar ratio is more preferably from about 0.005:1 to 0.20:1.

The process of the present invention is regioselective; methylmalonic acid is obtained without any succinic acid being detected.

Methylmalonic acid which is present, at least partially, in the form of its alkali or alkaline-earth metal salt at the end of carbonylation, is isolated from the reaction mixture by standard chemical methods (e.g. vapor phase chromatography).

These and other features and advantages of the present invention will be described more completely with reference to the following examples, which in no case may be regarded as limiting the invention.

DETAILED DESCRIPTION OF THE PREFERRED EMBODIMENTS

EXAMPLES 1 to 6

The solvent, as set forth in Table 1 below, was charged into a 250 cm$^3$ round bottomed glass flask equipped with a magnetic stirrer. The amount of alkali or alkali-earth metal hydroxide, as set forth in Table 1 below, was then added. Acrylic acid was introduced dropwise while stirring.

The reaction mixture was degassed by bubbling argon through the mixture for about 30 minutes. The argon atmosphere was purged using a gentle stream of carbon monoxide.

The reaction flask was then connected to a graduated burette filled with carbon monoxide at atmospheric pressure (0.1 MPa), creating a closed system.

Iron pentacarbonyl was added to the flask by injection through a septum using a syringe. The reaction flask was immersed in a thermostatted oil bath stabilized at a chosen temperature and integrally connected to a magnetic stirring plate (rotating at 750 revolutions/minute).

The progress of the reaction was followed by taking aliquot samples.

Determination of the yield using vapor phase chromatography was carried out with the aid of an internal standard (methyl isovalerate) after acidification with dilute HCl, treatment at 0° C. with an excess of diazomethane in solution in ethyl ether, and neutralization of the excess diazomethane.

The characteristics of each example and the results obtained after 48 hours of reaction are collated in Table 1.

TABLE 1

| Examples | Acrylic acid (in mmol) | Solvent in cm³ | | Bases in mmol | Fe(CO)₅ (mmol) | T °C. | Yld of MMA % |
|---|---|---|---|---|---|---|---|
| Ex. 1 | 8.9 | H₂O | 50 | KOH (18.3) | 1.4 | 60 | 51 |
| Ex. 2 | 9.0 | H₂O | 50 | KOH (18.5) | 1.4 | 70 | 65 |
| Ex. 3 | 8.8 | H₂O | 50 | LiOH (18.7) | 1.4 | 60 | 37 |
| Ex. 4 | 9.2 | H₂O | 50 | Ca(OH)₂ (15.2) | 1.4 | 70 | 66 |
| Ex. 5 | 19.2 | H₂O t-BuOH | 40 10 | Ca(OH)₂ (30.2) | 1.4 | 70 | 62 |
| Ex. 6 | 35.0 | H₂O iPrOH | 80 20 | Ca(OH)₂ (62) | 0.7 | 70 | 63 |

Abbreviations employed in Table 1
Yld of MMA % = % yield of methylmalonic acid based on the acrylic acid charged
t-BuOH = 2-methyl-2-propanol
iPrOH = 2-propanol

EXAMPLES 7 and 8

The method of Examples 1 to 6 was repeated except the methylmalonic acid was isolated at the end of the reaction (48 hours). The isolation treatment comprises cooling the final reaction mixture to approximately −25° C. and then separating, by filtration, insoluble part A which is calcium methylmalonate and calcium hydroxide from the filtrate B. The filtrate was stirred in air, overnight, and then filtered to remove the iron salts.

The new filtrate was added to the solid fraction A and the solution thus obtained was neutralized with dilute hydrochloric acid. This solution was then saturated with sodium chloride and was extracted with five 200 cm³ portions of ethyl ether.

The ethyl ether solution was dried over Mg sulphate by the evaporation of the solvent, at reduced pressure. The evaporated solvent contain unreacted acrylic acid and traces of propionic acid which were formed. After drying, a solid was recovered and weighed.

The purity of the methylmalonic acid was confirmed by proton NMR (60 MHz) in a solution of heavy water. The NMR is carried out in the presence of pyridinium hydrochloride as an internal standard.

The compositions of the two examples and the results obtained are set forth in Table 2 below.

TABLE 2

| Examples | Acrylic acid (in mmol) | Solvents in cm³ | | Ca(OH)₄ in mmol | Fe(CO)₅ (mmol) | T °C. | Yld of MMA % |
|---|---|---|---|---|---|---|---|
| Ex. 7 | 9.1 | H₂O t-BuOH | 40 10 | 23.6 | 1.4 | 70 | 80 |
| Ex. 8 | 35.3 | H₂O t-BuOH | 80 20 | 56.8 | 0.7 | 70 | 43 |

Abbreviations employed in Table 2
Yld of MMA % = % yield of methylmalonic acid based on the acrylic acid charged
t-BuOH = 2-methyl-2-propanol
iPrOH = 2-propanol

We claim:

1. A process for the preparation of methylmalonic acid comprising:
   reacting acrylic acid in basic solution with carbon monoxide and water in the presence of a catalytically effective amount of an iron carbonyl derivative or a compound capable of forming an iron carbonyl derivative in the reaction mixture.

2. The process of claim 1, wherein the iron carbonyl derivative is iron pentacarbonyl, Fe₂(CO)₉, or a compound of the formula $M^{n+}[HFe(CO)_4]_n-$ in which M is an alkali or alkaline-earth metal and n is 1 or 2.

3. The process of claim 1, wherein the iron carbonyl derivative is iron pentacarbonyl.

4. The process of claim 1, wherein the basic solution is an at least partially aqueous solution of an alkali metal or alkaline-earth metal hydroxide.

5. The process of claim 4, wherein the hydroxide is sodium hydroxide, potassium hydroxide, lithium hydroxide, calcium hydroxide, barium hydroxide, strontium hydroxide or magnesium hydroxide.

6. The process according to claim 5, wherein the hydroxide is calcium hydroxide.

7. The process according to claim 4, wherein the amount of hydroxide in the reaction mixture is from about 0.1 mole to 5 moles per liter of solvent.

8. The process according to claim 4, wherein the hydroxide in the reaction mixture is from 0.2 mole to 2 moles per liter of solvent.

9. The process of claim 1, wherein the solvent in said basic solution is water.

10. The process of claim 1, wherein the solvent in said basic solution is a mixture of water and a secondary or tertiary alcohol.

11. The process of claim 10, wherein the volume ratio of secondary or tertiary alcohol to water-alcohol mixture is from about 10% to 60%.

12. The process of claim 10, wherein the volume ratio of secondary or tertiary alcohol to water-alcohol mixture is from about 20% to 50%.

13. The process of claim 1, wherein the reaction temperature is equal to or higher than 50° C.

14. The process of claim 13, wherein the reaction temperature is from about 60° C. to 120° C.

15. The process of claim 1, wherein the reaction is carried out at a partial pressure of carbon monoxide from about 0.1 MPa to 1 MPa.

16. The process of claim 15, wherein the reaction is carried out at a partial pressure of carbon monoxide from about 0.1 MPa to 0.5 MPa.

17. The process of claim 1, wherein the amount of acrylic acid is from about 0.1 mole to 5 moles per liter of solvent.

18. The process of claim 1, wherein the molar ratio of iron carbonyl derivative to acrylic acid is from about 0.001:1 to 0.30:1.

19. The process of claim 18, wherein the molar ration of iron carbonyl derivative to acrylic acid is about 0.005:1 to 0.20:1.

* * * * *